(12) United States Patent
Bette et al.

(10) Patent No.: US 12,740,789 B2
(45) Date of Patent: Sep. 22, 2026

(54) MEDICAL DEVICES AND METHODS FOR PENETRATING AN ANATOMICAL STRUCTURE BASED ON SENSED ELECTRICAL CHARACTERISTICS

(71) Applicants: SpineGuard, Vincennes (FR); Sorbonne Universite, Paris (FR); Centre National de la Recherche Scientifique - CNRS, Paris (FR); INSERM (Institut National de la Sante et de la Recherche Medicale), Paris (FR)

(72) Inventors: Stephane Bette, Aix en Provence (FR); Jimmy Da Silva, Vincennes (FR); Thibault Chandanson, Vincennes (FR); Guillaume Morel, Paris (FR); Maurice Bourlion, Rive de Gier (FR)

(73) Assignees: Spine Gaurd, Vincennes (FR); Sorbonne Universite, Paris (FR); Centre National de la Recherche Scientifique—CNRS, Paris (FR); INSERM (Institut National de la Sante et de la Recherche Medicale), Paris (FR)

( * ) Notice: Subject to any disclaimer, the term of this patent is extended or adjusted under 35 U.S.C. 154(b) by 1179 days.

(21) Appl. No.: 17/661,719

(22) Filed: May 2, 2022

(65) Prior Publication Data

US 2022/0361896 A1 Nov. 17, 2022

(30) Foreign Application Priority Data

May 5, 2021 (FR) ...................................... 2104761

(51) Int. Cl.
*A61B 34/32* (2016.01)
*A61B 17/16* (2006.01)
*A61B 17/00* (2006.01)

(52) U.S. Cl.
CPC ............ *A61B 17/164* (2013.01); *A61B 34/32* (2016.02); *A61B 2017/00026* (2013.01); *A61B 2017/00119* (2013.01)

(58) Field of Classification Search
CPC ....... A61B 17/16; A61B 17/164; A61B 34/10; A61B 34/20; A61B 34/30; A61B 34/32
See application file for complete search history.

(56) References Cited

U.S. PATENT DOCUMENTS

| | | | |
|---|---|---|---|
| 5,334,205 | A | 8/1994 | Cain |
| 6,337,994 | B1 | 1/2002 | Stoianovici et al. |

(Continued)

FOREIGN PATENT DOCUMENTS

| | | | |
|---|---|---|---|
| CN | 1929789 | A | 3/2007 |
| CN | 103948412 | A | 7/2014 |

(Continued)

OTHER PUBLICATIONS

Int'l Search Report & Written Opinion dated Jan. 7, 2019 in Int'l PCT Patent Appl. Serial No. PCT/FR2018/052640.

(Continued)

*Primary Examiner* — Si Ming Ku
(74) *Attorney, Agent, or Firm* — Greenberg Traurig, LLP; Christopher C. Bolten; Albert K. Heng

(57) ABSTRACT

A medical device for penetrating a bone structure including a processing unit having a transfer function that associates an electrical conductivity value S with a depth value d, wherein the processing unit is configured to detect a threshold selected from amongst an absolute threshold, a relative threshold and a critical gradient, and to emit a warning (Continued)

signal and/or control signal responsive to detection of the threshold.

29 Claims, 6 Drawing Sheets

(56) References Cited

U.S. PATENT DOCUMENTS

| | | | |
|---|---|---|---|
| 6,470,207 | B1 | 10/2002 | Simon et al. |
| 6,635,062 | B2 | 10/2003 | Ray, III et al. |
| 6,796,985 | B2 | 9/2004 | Bolger et al. |
| 7,580,743 | B2 | 8/2009 | Bourlion et al. |
| 8,092,457 | B2 | 1/2012 | Oettinger et al. |
| 8,118,594 | B2 | 2/2012 | Pernot et al. |
| 8,221,428 | B2 | 7/2012 | Trieu |
| 8,361,152 | B2 | 1/2013 | McCormack et al. |
| 8,419,746 | B2 | 4/2013 | Bourlion et al. |
| 8,486,119 | B2 | 7/2013 | Bourlion |
| 8,634,897 | B2 | 1/2014 | Simon et al. |
| 8,795,285 | B2 | 8/2014 | Kwon |
| 8,939,979 | B2 | 1/2015 | Del et al. |
| 9,066,751 | B2 | 6/2015 | Sasso |
| 9,119,732 | B2 | 9/2015 | Schifano et al. |
| 9,204,830 | B2 | 12/2015 | Zand et al. |
| 9,538,935 | B2 | 1/2017 | Bourlion et al. |
| 9,855,060 | B2 | 1/2018 | Ardel et al. |
| 9,901,283 | B2 | 2/2018 | Bourlion et al. |
| 9,937,009 | B2 | 4/2018 | Schroeder et al. |
| 10,064,630 | B2 | 9/2018 | Forman et al. |
| 10,092,300 | B2 | 10/2018 | Del et al. |
| 10,149,729 | B2 | 12/2018 | Smaby et al. |
| 10,624,572 | B2 | 4/2020 | Bourlion et al. |
| 10,987,113 | B2 | 4/2021 | Mcginley et al. |
| 11,000,292 | B2 | 5/2021 | Mcginley |
| 11,058,436 | B2 | 7/2021 | Mcginley et al. |
| 11,083,469 | B2 | 8/2021 | Del et al. |
| 11,291,381 | B2 | 4/2022 | Bourlion et al. |
| 11,344,372 | B2 | 5/2022 | Bourlion et al. |
| 11,399,902 | B2 | 8/2022 | Bourlion et al. |
| 11,789,177 | B2 | 10/2023 | Hokstad |
| 11,903,591 | B2 | 2/2024 | Chen et al. |
| 12,161,348 | B2 | 12/2024 | Lorian et al. |
| 12,213,683 | B2 | 2/2025 | Del et al. |
| 12,458,367 | B2 | 11/2025 | Chandanson et al. |
| 2002/0120197 | A1 | 8/2002 | Kleffner et al. |
| 2003/0078495 | A1 | 4/2003 | Goodwin |
| 2003/0187348 | A1 | 10/2003 | Goodwin |
| 2005/0116673 | A1 | 6/2005 | Carl et al. |
| 2005/0119660 | A1 | 6/2005 | Bourlion et al. |
| 2006/0241628 | A1 | 10/2006 | Parak |
| 2006/0258951 | A1 | 11/2006 | Bleich et al. |
| 2007/0218420 | A1 | 9/2007 | Syribeys |
| 2007/0239187 | A1 | 10/2007 | Brunnett et al. |
| 2008/0086140 | A1 | 4/2008 | Wolf |
| 2008/0262526 | A1 | 10/2008 | Neubardt et al. |
| 2009/0157059 | A1 | 6/2009 | Allen et al. |
| 2010/0024981 | A1 | 2/2010 | Wallace et al. |
| 2010/0286694 | A1 | 11/2010 | Rio et al. |
| 2011/0015649 | A1 | 1/2011 | Anvari et al. |
| 2012/0046668 | A1 | 2/2012 | Gantes |
| 2012/0296213 | A1 | 11/2012 | Mauldin, Jr. et al. |
| 2013/0085413 | A1 | 4/2013 | Tsamir et al. |
| 2013/0085505 | A1 | 4/2013 | Markey et al. |
| 2013/0152746 | A1 | 6/2013 | Kerboul et al. |
| 2013/0172902 | A1 | 7/2013 | Lightcap et al. |
| 2013/0296734 | A1 | 11/2013 | Bourlion et al. |
| 2014/0094808 | A1 | 4/2014 | Herndon |
| 2014/0276002 | A1 | 9/2014 | West et al. |
| 2014/0276839 | A1 | 9/2014 | Forman et al. |
| 2014/0276950 | A1 | 9/2014 | Smaby et al. |
| 2014/0324044 | A1 | 10/2014 | Haufe et al. |
| 2015/0066030 | A1 | 3/2015 | Mcginley et al. |
| 2015/0148176 | A1 | 5/2015 | Schroeder et al. |
| 2015/0196306 | A1 | 7/2015 | Del et al. |
| 2015/0366624 | A1 | 12/2015 | Kostrzewski et al. |
| 2016/0012582 | A1 | 1/2016 | Mauldin, Jr. et al. |
| 2016/0074123 | A1 | 3/2016 | Bly et al. |
| 2016/0106392 | A1 | 4/2016 | Manbachi et al. |
| 2016/0302871 | A1 | 10/2016 | Gregerson et al. |
| 2016/0361069 | A1 | 12/2016 | Ardel et al. |
| 2016/0361070 | A1 | 12/2016 | Ardel et al. |
| 2017/0007199 | A1 | 1/2017 | Bourlion et al. |
| 2017/0056116 | A1 | 3/2017 | Kostrzewski |
| 2017/0100822 | A1 | 4/2017 | Cutler |
| 2017/0360493 | A1 | 12/2017 | Zucker et al. |
| 2018/0042514 | A1 | 2/2018 | Verard et al. |
| 2018/0098714 | A1 | 4/2018 | Bourlion et al. |
| 2018/0177556 | A1 | 6/2018 | Noonan |
| 2018/0242985 | A1 | 8/2018 | Vipperman et al. |
| 2019/0175886 | A1 | 6/2019 | Abdelwahed et al. |
| 2019/0201011 | A1 | 7/2019 | Del et al. |
| 2019/0388173 | A1 | 12/2019 | Pak et al. |
| 2020/0324408 | A1 | 10/2020 | Bourlion et al. |
| 2020/0337782 | A1 | 10/2020 | Glassman et al. |
| 2021/0068905 | A1 | 3/2021 | Quaid et al. |
| 2021/0282862 | A1 | 9/2021 | Bourlion et al. |
| 2021/0298795 | A1 | 9/2021 | Bowling et al. |
| 2022/0022891 | A1 | 1/2022 | Del et al. |
| 2022/0104901 | A1 | 4/2022 | Lawrie |
| 2022/0168048 | A1 | 6/2022 | Shoham et al. |
| 2022/0175455 | A1 | 6/2022 | Ungi et al. |
| 2022/0175462 | A1 | 6/2022 | Turgeman et al. |
| 2022/0218421 | A1 | 7/2022 | Junio et al. |
| 2022/0233250 | A1 | 7/2022 | Bette et al. |
| 2022/0361897 | A1 | 11/2022 | Chen et al. |
| 2022/0409214 | A1 | 12/2022 | Lorian et al. |
| 2023/0088846 | A1 | 3/2023 | Laing et al. |
| 2023/0095197 | A1 | 3/2023 | Chandanson et al. |
| 2023/0134461 | A1 | 5/2023 | Casey et al. |
| 2024/0237994 | A1 | 7/2024 | Chandanson et al. |

FOREIGN PATENT DOCUMENTS

| | | | | |
|---|---|---|---|---|
| CN | 107921554 | A | 4/2018 | |
| CN | 110882037 | A | 3/2020 | |
| CN | 118251181 | A | 6/2024 | |
| DE | 102010042012 | A1 | 4/2012 | |
| DE | 102011083360 | A1 | 3/2013 | |
| EP | 1474046 | A1 | 11/2004 | |
| EP | 3319539 | A1 | 5/2018 | |
| EP | 3525696 | A1 | 8/2019 | |
| EP | 3761870 | A1 | 1/2021 | |
| EP | 3883491 | A1 | 9/2021 | |
| FR | 2795624 | A1 | 1/2001 | |
| FR | 3034643 | A1 | 10/2016 | |
| JP | 2005525150 | A | 8/2005 | |
| JP | 2016518878 | A | 6/2016 | |
| WO | WO-03068076 | A1 | 8/2003 | |
| WO | WO-2014146090 | A1 | 9/2014 | |
| WO | WO-2015006296 | A1 | 1/2015 | |
| WO | WO-2016043676 | A1 | 3/2016 | |
| WO | WO-2016162634 | A1 | 10/2016 | |
| WO | WO-2016199152 | A1 | 12/2016 | |
| WO | WO-2019002578 | A1 | 1/2019 | |
| WO | WO-2019081850 | A1 * | 5/2019 | ............. A61B 5/063 |
| WO | WO-2019110119 | A1 | 6/2019 | |
| WO | WO-2020000038 | A1 | 1/2020 | |
| WO | WO-2020097481 | A1 | 5/2020 | |
| WO | WO-2021046247 | A1 | 3/2021 | |
| WO | WO-2021111439 | A1 | 6/2021 | |
| WO | WO-2021178706 | A1 | 9/2021 | |
| WO | WO-2022170185 | A1 | 8/2022 | |

OTHER PUBLICATIONS

International Search Report & Written Opinion dated Aug. 31, 2022 in Int'l PCT Patent Appl. Serial No. PCT/EP2022/061868.

Aly, et al. "On ultrasound imaging for guided screw insertion in spinal fusion surgery," Ultrasound in Medicine & Biology, vol. 37(4): 651-664 (Jan. 2011).

Balmer, et al., Characterization of the Electrical Conductivity of Bone and Its Correlation to Osseous Structure, Scientific Reports, 8:8601 (2018).

(56) References Cited

OTHER PUBLICATIONS

Chang, et al. "Proof of concept: in vitro measurement of correlation between radiodensity and ultrasound echo response of ovine vertebral bodies," Ultrasonics, vol. 51(3): 253-257 (2011).
International Preliminary Report on Patentability for International Application No. PCT/IL2020/051241, mailed Jun. 16, 2022, 10 pages.
International Search Report & Written Opinion dated Oct. 1, 2024 in Int'l PCT Patent Appl. Serial No. PCT/EP2024/017206.
International Search Report & Written Opinion dated Dec. 15, 2022 in Int'l PCT Patent Appl. No. PCT/IB2022/059201.
International Search Report and Written Opinion for PCT Application No. PCT/IL2020/051241, mailed Mar. 22, 2021, 13 pages.
International Search Report and Written Opinion for PCT Application No. PCT/IL2022/050585, mailed Nov. 3, 2022, 15 pages.
International Search Report for PCT Application No. PCT/FR2015/050241 mailed May 4, 2015, 08 Pages.
Kantelhardt, et al. "Intra-osseous ultrasound for pedicle screw positioning in the subaxial cervical spine: an experimental study," Acta Neurochirurgica, vol. 152(4):655-661, (2010).
Kantelhardt, et al. "Intraosseous ultrasonography to X determine the accuracy of drill hole positioning prior to the placement of pedicle screws: an experimental study," Journal of Neurosurgery: Spine, vol. 11(6): 673-680, (Dec. 2009).
Kantelhardt, et al. "Intraosseous Ultrasound in the Placement of Pedicle crews in the Lumbar Spine," Spine, vol. 34(4): 400-407, (2009).
Lou, E., Zhang, C., Le, L., Hill, D., Raso, J., Moreau, M & Hedden, D. (2010). Using ultrasound to guide the insertion of pedicle screws during scoliosis surgery. In Research into Spinal Deformities 7 (pp. 44-48). IOS Press. (Year: 2010).
Manbachi, et al. "Guided pedicle screw insertion: techniques and training," The Spine Journal, vol. 14(1): 165-179 (Year: 2014).
Mujagic, et al., "Development of a method for ultrasound-guided placement of pedicle screws," IEEE Transactions on Ultrasonics, Ferroelectrics, and Frequency Control, vol. 55(6): 1267-1276 (Jun. 2008).
Raphael, et al. "A-Mode ultrasound guidance for pedicle screw advancement in ovine vertebral bodies," The Spine Journal, vol. 10(5): 422-432, (Feb. 2010).
Yamada, M., Moriya, H., lino, T., Kasai, Y., Sudo, A., & Uchida, A. (2012). Ultrasonic measurement of bone thickness for spinal surgery. IEEE transactions on ultrasonics, ferroelectrics, and frequency control, vol. 59(9), 2077-2088 (Sep. 2012).

* cited by examiner

MEDICAL DEVICES AND METHODS FOR PENETRATING AN ANATOMICAL STRUCTURE BASED ON SENSED ELECTRICAL CHARACTERISTICS

CROSS-REFERENCE TO RELATED APPLICATIONS

This application claims the benefit of priority of French Patent Application Serial No. 2104761, filed May 5, 2021, the entire contents of which are incorporated herein by reference.

FIELD OF USE

The present disclosure relates to a medical device for penetrating an anatomical structure, a medical system comprising such a medical device, and methods of use.

BACKGROUND

The principles of the present invention apply to any type of surgical intervention on an anatomical structure made up of anatomical media having different electrical conductivities.

The invention nonetheless applies very particularly in orthopedic surgery and in surgery of the spine, in which one or more penetrating medical devices are used by a surgeon to penetrate an anatomical structure comprising a bone structure and, in particular, to drill bone structure, for example to position or attach a prosthesis or an implant.

Among the bone structures on which the surgeon may operate, some include an outer layer of cortical bone enclosing a layer of trabecular bone, the layer of trabecular bone at least partially covering a layer of internal cortical bone. The anatomical structure also may include soft tissues bordered by the layer of internal cortical bone which then forms an interface between the layer of trabecular bone and the soft tissues. During a procedure, it is important to prevent damage to functional tissues, such as tissues of the nervous or vascular system, located near the outer cortical bone layer or in soft tissues. This is particularly the case for an intervention on a vertebral pedicle in which the nerve roots are close to the outer cortical bone layer and the spinal cord constitutes part of the soft tissues bordered by the internal cortical bone layer forming the vertebral foramen.

To assist the surgeon in preventing damage to functional tissues, it is known to obtain information on positioning of the penetrating medical device, e.g., drill bit, with respect to the different anatomical media of the anatomical structure based on their respective electrical conductivities, which are representative of the ability of the media to conduct an electric current. The layer of trabecular bone and the soft tissues constitute first and second anatomical media respectively having first and second electrical conductivities, the first electrical conductivity being lower than the second electrical conductivity. The cortical bone layer constitutes a third anatomical medium and has a third electrical conductivity, lower than the first and second electrical conductivities.

Hand tools are known in medical applications for exploiting differences in electrical conductivity of the media comprising a bone structure. For example, the manually manipulated medical device marketed under the name of PediGuard®, described in document WO 03/068076, uses such differences to vary a warning signal perceptible by the surgeon, so to alert the surgeon when damage to functional tissue is occurring or is imminent.

The differences in electrical conductivity of the media of the anatomical structure comprising a bone structure have also been exploited in medical applications implementing an at least partially automated medical system subject in part to automatic control, and in particular, in robotics. For example, the medical system described in WO 2019/081850, uses these differences to vary a warning signal used in a control signal controlling movement of a robotic arm and to modify the control signal when the warning signal indicates that damage to functional tissue is occurring or imminent.

Although these foregoing systems are beneficial, it would be desirable to provide systems and methods that offer improved precision and more reliable discrimination of anatomical media during the penetration into an anatomical structure comprising a bone structure, thereby to better ensure patient safety. Such improved systems and methods will find applicability in any intervention on any type of anatomical structure, whether or not it requires penetrating a bone structure.

SUMMARY OF THE INVENTION

In accordance with the principles of the present invention, systems, devices and methods are provided for penetrating an anatomical structure having anatomical media with difference electrical conductivities, wherein a warning signal is generated that predicts imminent penetration and/or actual penetration into functional tissues, so as avoid damage thereto.

In a first embodiment, a medical device is provided for penetrating an anatomical structure consisting of anatomical areas having different electric conductivities, wherein the electrical conductivities of each of the media fall within defined ranges. More specifically, the medical device includes:

- a body configured to penetrate into the anatomical structure, the body having an outer surface, a longitudinal axis, a distal end configured to contact the anatomical structure, and a proximal end opposite the distal end,
- at least a first electrode having a first contact surface disposed at the distal end on the outer surface of the body to contact with the anatomical structure,
- at least a second electrode having a second contact surface disposed at distal end of outer surface of the body to contact the anatomical structure at a location spaced apart from the first contact surface,
- a processing unit including an electrical measurement unit configured to measure at least one electrical characteristic A representative of the electrical conductivity S of the anatomical medium between the first and second contact surfaces, the electrical characteristic A being associated with the electrical conductivity S by a transfer function T such that S=T (A), and a depth sensing unit configured to determine a depth at which the distal end of the body has entered the anatomical structure, wherein the processing unit is configured to compute evolution of electrical characteristic values as a function of depth values.

In accordance with the present invention, the processing unit further is configured to emit a warning signal when the evolution of the values of electrical characteristic as a function of the depth satisfies at least one of the following criteria:

crossing a conductivity threshold: the processing unit is configured to determine whether the electrical characteristic value crosses a conductivity threshold selected from an absolute conductivity threshold: $N_a \times Ds$, where Ds is within a range of electrical characteristic values between predefined minimum and maximum electrical characteristics, and $N_a$ is a real number between 0 and 1, and a relative conductivity threshold: $N_r \times MS(d)$ where MS is an average of the electrical characteristic values between an initial depth value and a current depth value d, and $N_r$ is a real number between 0 and 5, crossing of a critical conductivity gradient: the processing unit is configured to determine that at least one slope p(d) of the evolution of the electrical characteristic value as a function of the depth crosses at least one critical conductivity gradient, representing a change from a first anatomical medium having a first electrical conductivity towards a second anatomical medium having a second electrical conductivity. The slope p(d) in milli-Siemens per meter per millimeter is computed as:

$$p(d) = \frac{T[A(d)] - T[A(d - k \times E_c)]}{k \times E_c}$$

where

T[A(d)] is the electrical conductivity in milli-Siemens per meter associated with the transfer function T for the value of electrical characteristic A at depth d, $T[A(d-k\times E_c)]$ is the electrical conductivity in milli-Siemens per meter associated with the transfer function T for the value of electrical characteristic A at the depth $d-k\times E_c$ located at a distance $k\times E_c$ from depth d, $E_c$ corresponds to a representative thickness, for example, of a third anatomical medium (e.g., cortical bone layer thickness) in millimeters, k is a positive real number between 0 and 5.

Accordingly, the invention employs one or more specific criteria, such as thresholds and/or variations of a measurement of the electrical characteristic as a function of depth, which criteria are particularly representative of the media of the anatomical structure in the vicinity of the distal end of the body. The use of the foregoing criteria may be direct, for example, when the electrical characteristic measured corresponds directly to electrical conductivity, or indirect, such as when the electrical characteristic measured is representative of, but different from, electrical conductivity and is associated to electrical conductivity by the transfer function. In the latter case, the criteria may be verified by reducing the electrical characteristic to electrical conductivity using the transfer function.

Each of the foregoing criterion may be employed alone or in combination with one or more of the other criteria. Combination of criteria may be performed in any suitable manner and in particular, in a non-binary context, such as by using fuzzy logic. In this case, evaluation of the criteria may be performed by continuously evaluating a degree of satisfaction between 0 (condition not satisfied in a certain way) and 1 (condition satisfied in a certain way), and a fuzzy inference, thus making possible the application of AND and OR logical reasoning to produce a conclusion with some degree of certainty. So-called Bayesian inference (or probabilistic) systems also may be used to implement this type of logical reasoning in the presence of uncertainty or noise in the conductivity measurement.

The processing unit may be configured to verify the criterion for crossing the critical conductivity gradient with one of the following conditions:

increase in conductivity, if the second electrical conductivity is greater than the first electrical conductivity:

$$p(d) > \frac{C \times Ds}{1 \text{ mm}}$$

where

C is a real number between 0 and 10, decrease in conductivity, if the second electrical conductivity is lower than the first electrical conductivity:

$$p(d) < \frac{C' \times Ds}{1 \text{ mm}}$$

where

C' is a real number between −10 and 0.

Thus, the criterion for crossing the critical conductivity gradient may correspond either to a predefined increase or a decrease in electrical conductivity.

When the medical device is designed to penetrate an anatomical structure that includes a third anatomical medium that constitutes an interface between the first and second anatomical mediums and has a third electrical conductivity, such as cortical bone, the processing unit may be configured to verify the criterion for crossing the critical conductivity gradient with a conductivity variation condition such as:

if the third conductivity is lower than the first and second electrical conductivities:

$$p(d_1) < \frac{C_1 \times Ds}{1 \text{ mm}}$$

and $$p(d_2) > \frac{C_2 \times Ds}{1 \text{ mm}}$$

where $p(d_1)$ is the slope at depth $d_1$, $C_1$ is a real number between −10 and 0, $p(d_2)$ is the slope at depth $d_2$ greater than $d_1$, $C_2$ is a real number between 0 and 10, if the third conductivity is greater than the first and second electrical conductivities:

$$p(d_1) > \frac{C_3 \times Ds}{1 \text{ mm}}$$

and $$p(d_2) < \frac{C_4 \times Ds}{1 \text{ mm}}$$

where $C_3$ is a real number between 0 and 10, $C_4$ is a real number between −10 and 0.

Thus, the criterion for crossing the critical conductivity gradient may correspond to a decrease in electrical conductivity followed by an increase in electrical conductivity in consecutive measurements if the third conductivity is lower than the first and second electrical conductivities, or to an increase in electrical conductivity followed by a decrease in electrical conductivity in consecutive measurements if the third conductivity is greater than the first and second electrical conductivities.

The processing unit may be configured to check the conductivity variation if depth values $d_1$ and $d_2$ have a maximum deviation e such that $e=m\times E_c$, where m is a positive real number between 0 and 80.

The foregoing arrangement establishes an interval beyond which a decrease in electrical conductivity and an increase in electrical conductivity are dissociated and thus do not confirm a variation in electrical conductivity.

The medical device may be designed to penetrate an anatomical structure that has a bone structure and soft tissues, wherein the bone structure includes a layer of trabecular bone constituting a first anatomical medium and a layer of cortical bone constituting a third anatomical medium, and the soft tissues constitute a second anatomical medium, such that the second electrical conductivity is greater than the first electrical conductivity and the third electrical conductivity is less than the first and second electrical conductivities.

The processing unit may be configured to define a plurality of critical conductivity gradients based on the average of the electrical characteristic values MA.

In preferred embodiments, the body of the medical device is configured to penetrate a bone structure, and may be configured to drill into the bone structure.

The penetrating body of the medical device may be selected from a drill, threaded tool, screw, implant, needle, cutting blade, nail, osteotome, burr, pin, probe, square tip, spatula, curette, tap or any other tool of suitable shape for penetrating the anatomical structure.

According to another aspect of the invention, there is proposed a medical system having:

- a penetrating medical device as defined above,
- a medical device comprising a base and end effector, e.g., on which the penetrating medical device is mounted, the medical device being configured to allow movement of the arm relative to the base, wherein the processing unit includes a force measurement unit configured to determine a force exerted on the body of the penetrating medical device, and wherein the processing unit is configured to control the displacement of the end effector relative to the base responsive to a setpoint force.

The invention thus controls the force applied to the penetrating medical device during displacement of the end effector.

The medical system may be configured for drilling an anatomical structure of an individual whose trunk is subject to periodic motion due to respiration, such that the processing unit may include a position determining unit configured to determine a position of the end effector relative to the base. More particularly, the processing unit may be adapted to measure a periodic amplitude of respiration, with the depth sensing unit being adapted to determine the depth to which the distal end of the body has entered anatomical structure by subtracting the periodic amplitude of respiration from the position of the end effector.

In this manner, the force control may be used to determine the depth of penetration of the body.

The processing unit can be configured to change the setpoint force based on the warning signal.

The present invention is particularly advantageous, but not exclusively, for controlling a robotic arm. In this case, the medical device may be a robotic arm comprising at least one articulation connecting the end effector to the base, the base configured to rest on a support surface.

The invention also may find applications in other embodiments, such as at least partially automated medical systems and hand-held tools. The medical device may be a hand-held tool, the base being configured to form a handle that is held by hand by an operator.

The body of the penetrating medical device may form a drill bit, the outer surface of which is provided with a thread, with the medical system further comprising a member for driving the drill bit in rotation along the body axis.

The invention as defined above may be implemented in a method of penetrating an anatomical structure consisting of media having different electrical conductivities falling within a range of electrical conductivities, the method including:

- measuring at least one representative electrical characteristic A of an electric conductivity S of an anatomical medium between first and second contact surfaces, respectively of first and second electrodes arranged at a distance from each other on an outer surface of a distal end of a body, the electrical characteristic A being associated with the electrical conductivity S by a transfer function T, such that S=T(A),
- determining a depth at which the end distal part of the body has penetrates the anatomical structure,
- following an evolution of electrical characteristic values according to depth values, and
- issuing a warning signal when at least one of the following criteria is verified:
- crossing a conductivity threshold: the processing unit is configured to determine that the electrical characteristic value crosses a conductivity threshold chosen from
  - an absolute conductivity threshold: $N_a\times Ds$, where Ds is a range of electrical characteristic values between the minimum and maximum electrical characteristics, and $N_a$ is a real number between 0 and 1, and
  - a relative conductivity threshold: $N_r\times MA$ (d) where MA is an average of the electrical characteristic values between an initial depth value and a current depth value d, and $N_r$ is a real number between 0 and 5,
- crossing a critical conductivity gradient: the processing unit is configured to determine that at least one slope p(d) of the evolution of the electrical characteristic values as a function of depth crosses at least one critical conductivity gradient representing a change from a first anatomical medium having a first electrical conductivity to a second anatomical medium having a second electrical conductivity. The slope p(d) in milli-Siemens per meter per millimeter is computed as:

$$p(d)=\frac{T[A(d)]-T[A(d-k\times E_c)]}{k\times E_c}$$

where

- T[A (d)] is the electrical conductivity in milli-Siemens per meter associated with the transfer function T for the value of electrical characteristic A at depth d,
- T [A ($d-k\times E_c$)] is the electrical conductivity in milli-Siemens per meter associated with the transfer function T for with the value of electrical characteristic A at the depth $d-k\times E_c$ located at a distance $k\times E_c$ from depth d, $E_c$ is a thickness of the third anatomical medium in millimeters, and k is a positive real number between 0 and 5.

The inventive method may provide for monitoring the criterion for crossing the critical conductivity gradient with one of the following conditions:

condition of increase in conductivity if the second electrical conductivity is greater than the first electrical conductivity:

$$p(d) > \frac{C \times Ds}{1\text{ mm}}$$

where

C is a real number between 0 and 10, conductivity reduction condition if the second electrical conductivity is lower than the first electrical conductivity:

$$p(d) < \frac{C' \times Ds}{1\text{ mm}}$$

where

C' is a real number between −10 and 0.

The method also may provide for penetrating an anatomical structure including a third anatomical medium that constitutes an interface between the first and second anatomical mediums and has a third electrical conductivity, such that the criterion for crossing the critical conductivity gradient may be configured to verify with a conductivity variation condition of such as:

if the third conductivity is lower than the first and second electrical conductivities:

$$p(d_1) < \frac{C_1 \times Ds}{1\text{ mm}}$$

and $$p(d_2) > \frac{C_2 \times Ds}{1\text{ mm}}$$

where $p(d_1)$ is the slope at a depth value $d_1$, $C_1$ is a real number between −10 and 0, $p(d_2)$ is the slope at a depth value $d_2$ greater than $d_1$, $C_2$ is a real number between 0 and 10, if the third conductivity is greater than the first and second electrical conductivities:

$$p(d_1) > \frac{C_3 \times Ds}{1\text{ mm}}$$

and $$p(d_2) < \frac{C_4 \times Ds}{1\text{ mm}}$$

where $C_3$ is a real number between 0 and 10, $C_4$ is a real number between −10 and 0.

The method may provide for checking the conduction variation condition if depth values $d_1$ and $d_2$ have a maximum difference e such that $e=m\times E_c$, where m is a positive real number between 0 and 80.

The method thus provides for penetrating an anatomical structure that has a bone structure and soft tissues, wherein the bone structure includes a layer of trabecular bone constituting a first anatomical medium and a layer of cortical bone constituting a third anatomical medium, and soft tissues constitute a second anatomical medium, such that the second electrical conductivity is greater than the first electrical conductivity and the third electrical conductivity is less than the first and second electrical conductivities.

The method thus may include drilling into a bone structure.

The method also may provide for defining a plurality of critical conductivity gradients as a function of the average of the electrical characteristic values MA.

The method of the present invention may be implementing with a medical device having a base and an end effector, the medical device being configured to allow movement of the end effector relative to the base, with the body being mounted on the end effector, the method further including determining a force exerted on the body, and controlling the displacement of the end effector relative to the base with a setpoint force.

The inventive method also may include drilling an anatomical structure of an individual whose trunk is subject to periodic motion due to respiration, such that the method may include determining a position of the end effector relative to the base, measuring a periodic amplitude of respiration and determining the depth to which the distal end of the body has penetrated the anatomical structure by subtracting the periodic amplitude of respiration from the position of the end effector.

The method also may provide for modifying the setpoint force as a function of the warning signal.

BRIEF DESCRIPTION OF THE DRAWINGS

Other characteristics, details and advantages will become apparent upon reading the following detailed description, and upon analyzing the appended drawings, in which.

DETAILED DESCRIPTION

Figures 1, 2:
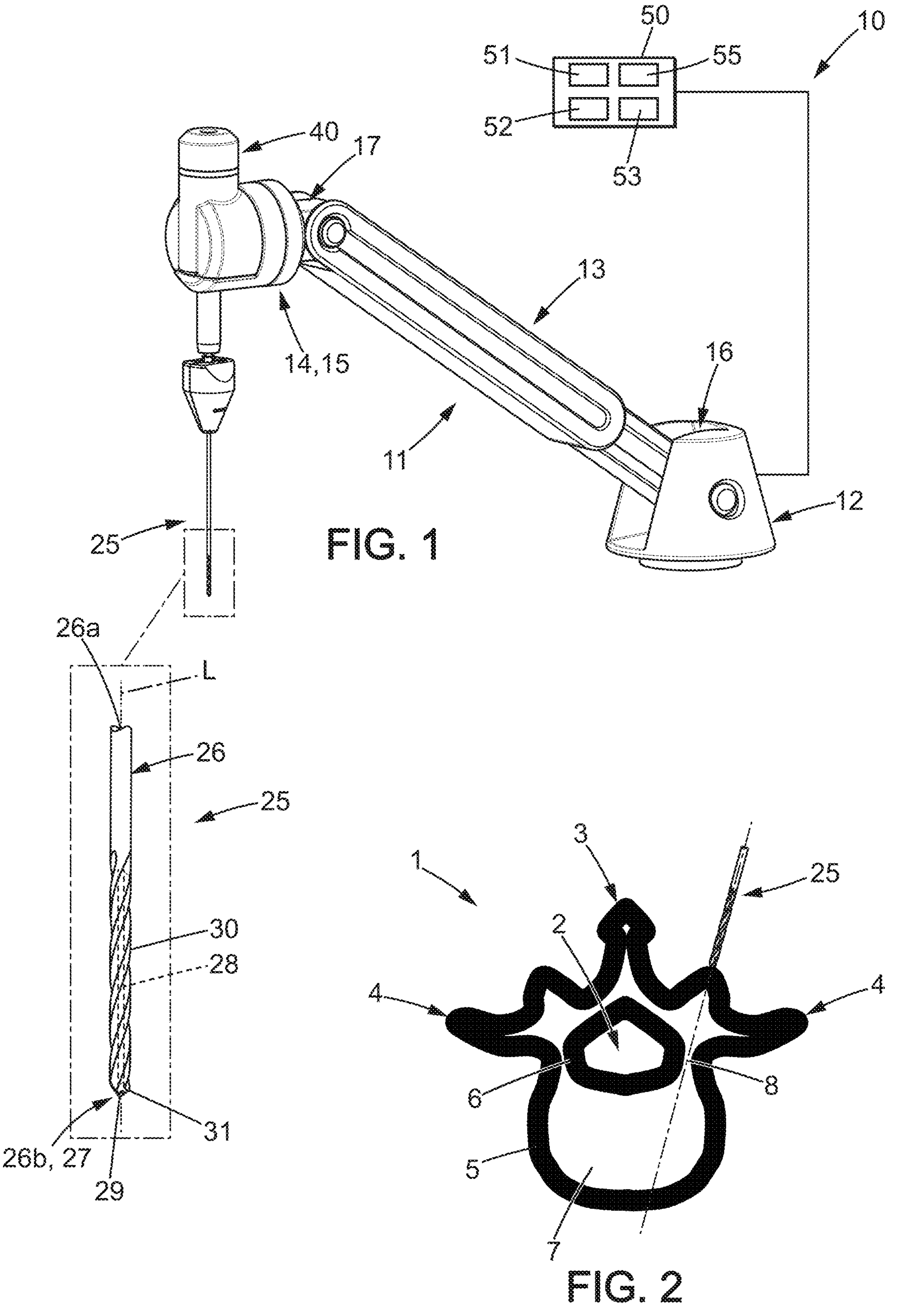
FIG. 1 depicts a first embodiment of a medical system in which a penetrating medical device is mounted on a robotic arm, the penetrating medical device being configured to penetrate an anatomical structure and measure an electrical characteristic, e.g., representative of the electrical conductivity of anatomical media of the anatomical structure, between first and second contact surfaces spaced apart from one another on a distal end of an exterior surface of a body, wherein the medical device is configured to emit a warning signal when an evolution of electrical characteristic value as a function of depth satisfies one or more predetermined criteria.
FIG. 2 depicts use of the medical system of FIG. 1 to drill an anatomical structure including a bone structure, such as a vertebra.

Referring to FIG. 1, illustrative medical system 10 constructed in accordance with the principles of the present invention is described.

Without being limited thereto, medical system 10 is particularly applicable to the field of orthopedic surgery and spine surgery, and provides a surgeon with assistance during a surgical procedure to place an implant on one or more vertebrae of a patient's spine.

Referring now also to FIG. 2, vertebra 1 is an anatomical structure that includes a bone structure. In particular, the bone structure internally has foramen 2 through which the spinal cord and vascular structures pass, spinous process 3 extending from a dorsal surface in a sagittal plane and two transverse processes 4 that extend substantially on either side of foramen 2 in a frontal plane, in the vicinity of which pass the nerve structures. Vertebra 1 is bounded on the outside by a layer of outer cortical bone 5. Foramen 2 is itself bounded by a layer of inner cortical bone 6. Between the layers of outer cortical bone 5 and inner cortical bone 6 is a layer of trabecular bone 7. Soft tissue and fluids, such as blood, surround outer cortical bone layer 5 and also are housed inside area bounded by inner cortical bone layer 6. Layer of trabecular bone 7 and the soft tissues constitute first and second anatomical media having respectively first and second electrical conductivities representative of the capacities of these respective anatomical media to conduct an electric current. The first electrical conductivity is lower than the second electrical conductivity. The inner and outer cortical bone layers constitute a third anatomical medium having a third electrical conductivity representative of the capacity of this anatomical medium to conduct electrical current, the third electrical conductivity being lower than the first and second electrical conductivities.

Still referring to FIG. 1, medical system 10 includes a medical device in the form of robotic arm 11 and penetrating medical device 25. Medical system 10 may be arranged to control of the movements of the surgeon to improve the precision and prevent the risk of damage to particularly sensitive functional tissues, such as the spinal cord, nerve structures and vascular structures. The assistance in controlling the surgical movements offered by medical system 10 may be partial, for example, by controlling only part of the surgeon's gestures, total, by entirely controlling the movement of robotic arm 11 and penetrating medical device 25, in place of the surgeon, or a combination of the two, e.g., alternating between full and partial control.

Robotic arm 11 includes base 12 configured to rest on a support surface, and end effector 14 arranged at an end opposite to base 12. Robotic arm 11 is configured to allow movement of end effector 14 relative to base 12. In particular, robotic arm 11 may comprise several segments interconnected by one or more joints. In the embodiment shown, a first segment constitutes base 12 on which a first end of second segment 13 is mounted by means of first articulation 16 having an appropriate number of degrees of freedom. Third segment 15, which carries end effector 14, is mounted on the second end of second segment 13 by means of second articulation 17, which also has an appropriate number of degrees of freedom. At least one of articulations 16, 17 is equipped with at least one actuator. For co-manipulation applications, the actuators of the joints may be reversible, that is to say, the joints allow a relative displacement of the segments with respect to each other under the effect of an external action exerted on robotic arm 11 by a user of the robotic arm and, in particular, the surgeon.

Penetrating medical device 25 includes body 26 designed to penetrate an anatomical structure and, in particular, a bone structure. When penetrating a vertebra, it is important to ensure precise positioning of the trajectory of body 26 of penetrating medical device 25 to avoid damaging or crossing cortical bone interface 6 that delimits foramen 2, or cortical bone layer 5 in the vicinity of the nerve structures. Penetrating medical device 25 therefore is configured to emit a variable warning signal depending on the electrical conductivity sensed as it is moved in the vertebra.

Without being limited thereto, the penetrating medical device may be a drill bit operating according to a principle analogous to that of the hand tool described in patent application WO 03/068076 and marketed under the name PediGuard®.

As shown in the inset to FIG. 1, body 26 extends along body axis L between proximal end 26*a* and distal end 26*b*, forming tip 27 configured to penetrate vertebra 1. Body 26 has a generally cylindrical outer surface, of circular section around body axis L, and may include a thread consisting of one or more helical cutting edges in the vicinity of tip 27. Body 26 could, however, have any other suitable shape, for example, cylindrical with a polygonal or other section. Alternatively, penetrating medical device 25 could form any other medical or surgical tool or instrument having a body configuration suitable for penetrating or drilling a bone structure. The penetrating medical device could in particular be chosen from among a threaded tool, a screw, an implant, a needle, a cutting blade, a nail, an osteotome, a burr, a pin, a probe, a square tip, a spatula, a curette and a tap.

Penetrating medical device 25 has first electrode 28, cylindrical in shape and formed of conductive material, extending inside body 26 parallel to axis L of the body. In particular, first electrode 28 may be disposed in a central bore of body 26 and extends coaxially with axis L of the body up to a free end having first contact surface 29, which is flush with an outer surface of body 26 at tip 27.

Penetrating medical device 25 also has second electrode 30, annular in shape and made of a conductive material, extending along axis L of the body around first electrode 28. In particular, second electrode 30 may be formed by part of body 26 and made of a conductive material. Second electrode 30 has second contact surface 31 including a cylindrical portion parallel to axis L of the body, corresponding to a lateral surface of body 26, and an annular portion transverse to axis L of the body, corresponding to a distal surface of body 26.

A layer of electrically insulating material, not shown, is interposed between first 28 and second 30 electrodes so that first 29 and second 31 contact surfaces contact tissues or bone at a distance spaced apart from each other during penetration of body 26 into vertebra 1.

The invention is not however limited to the previously described configuration of body 26, of first 28 and second 30 electrodes or the layer of electrically insulating material. For example, first 28 and second 30 electrodes may be non-coaxially arranged, for example, and each may be made of a rod of conductive material embedded in body 26. Furthermore, first electrode 28 and second electrode 30 may each have a point contact surface 29, 31 or the like flush with the lateral surface or the distal surface of body 26, in the vicinity of distal end 26*b*. Body 26 further could support two or more than two first electrodes 28 and two or more than two second electrodes 30.

Medical system 10 further comprises a drive member, such as a geared motor assembly, configured to drive body 26 in rotation along the axis L of the body. In a first mode of embodiment, the drive member may be mounted in housing 40 secured to end effector 14 of robotic arm 11 so that once secured to the drive member, body 26 of penetrating medical device 25 is mounted on end effector 14 of robotic arm 11.

As indicated previously, penetrating medical device 25 emits a variable warning signal depending on sensed electrical conductivity. To accomplish this, penetrating medical device 25 includes processing unit 50 configured to follow an evolution of electrical characteristic values as a function of depth values, wherein the electrical characteristic is chosen to be representative of the electrical conductivity of the medium between first 29 and second 31 contact surfaces. Thus, each depth value is associated with a single electrical characteristic value determined as described below. Processing unit 50, may be a generic processor-based controller programmed as described in this disclosure or may alternatively comprise a purpose-built controller to accomplish the described functions.

Processing unit 50 includes depth detection unit 51 configured to determine a depth at which distal end 26*b* of body 26 has advanced into an anatomical structure, such as vertebra 1. This depth corresponds to a distance in mm traveled into the bone structure by distal end 26*b* of body 26 in a drilling direction parallel to axis L of the body, between an initial instant to and a current instant t. The initial time to may be chosen in many different ways, for example, at the start of data recording or the time at which tip 27 of body 26 contacts cortical bone layer 5. Alternatively, the initial time may be logged as the time a drilling depth do is reached beyond the first contact with the layer of cortical bone 5. The instant to also may be defined as corresponding to the end of the lapse of a given time, e.g. using a timer, after any of these trigger events is detected.

According to a particularly advantageous, but non-limiting, embodiment, the depth of travel of tip 27 may be determined from force-controlled displacement of end effector 14 of robotic arm 11 relative to base 12. To do this, processing unit 50 is configured to control movement of the end effector 14 relative to the base 12 with a setpoint force. Processing unit 50 may then include:

- force measurement unit 52 configured to determine, by any suitable means, a force exerted on body 26, and
- position determination unit 53 configured to determine a position of end effector 14 of robotic arm 11 relative to base 12.

For example, processing unit 50 may impose a setpoint force with a non-zero component along axis L of the body and zero components along axes perpendicular to the axis. During penetration, displacement of end effector 14 then is controlled so as to have the non-zero component along the axis of the body, and to cancel out components along the other axes.

With regard to drilling of vertebra 1 belonging to the trunk of an individual whose respiration causes periodic movements, a periodic amplitude of respiration may be measured initially by processing unit 50. For example, tip 27 of body 26 may rest freely on vertebra 1 or any other part of the patient's body undergoing a displacement analogous to that of vertebra 1 due to breathing. Position determining unit 53 then measures the amplitude of displacement of body 26 of penetrating medical device 25 and of end effector 14. By maintaining a constant setpoint force on penetrating medical device and end effector 14, depth detection unit 51 can thereby determine depth to which distal end 26*b* of body 26 has entered vertebra 1 by subtracting the periodic amplitude of respiration from the position of end effector 14.

In other embodiments, the depth may be determined in any other suitable manner, for example, by a direct measurement of the depth using an external depth detection unit, a graduation on an external surface of the body 26, or a rod slidably mounted near body 26.

Processing unit 50 also includes electrical measurement unit 55 configured to measure, continuously and in real time, one or more electrical characteristics representative of the electrical conductivity of the medium between first contact surface 29 and second contact surface 31. Electrical characteristic A sensed by the contact surfaces then may be directly associated with electrical conductivity S by a known transfer function T such that S=T (A). In the embodiment shown, the electrical characteristic corresponds directly to the electrical conductivity S, such that transfer function T is an identity function. Alternatively, the electrical characteristic measured may be any other value, for example:

- an electrical resistivity or an electrical impedance, wherein transfer function T is an inverse function of type K(1/A),
- a conductance, an electrical voltage or an electrical intensity, wherein transfer function T is a proportional or linear function, or
- any measurement that can be linked to the electrical conductivity by a transfer function T previously defined in any appropriate manner, such as by calibration, testing, learning of the artificial intelligence type, collection of data in the literature or other, for example a coupled measurement of amplitude and phase at different frequencies, a combination of one or more of the aforementioned electrical characteristics and their associated transfer function.

Processing unit 50 then may follow a change in electrical characteristic values as a function of depth values.

Referring now to FIGS. 3 to 10, exemplary criteria are described so that processing unit 50 emits a warning signal when one or more of the criterion are verified to occur.

Figure 3:
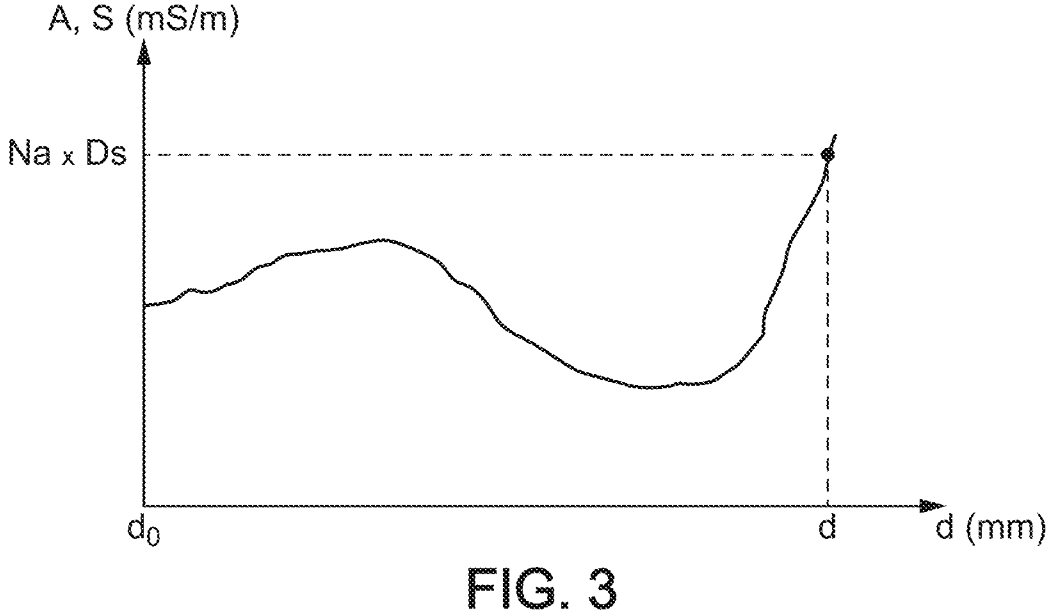
FIG. 3 is a graph depicting the evolution of an electrical characteristic value as a function of depth for use in verifying a criterion for crossing an absolute conductivity threshold, wherein the electrical characteristic is electrical conductivity and the value of electrical characteristic at the depth value d crosses and exceeds an absolute conductivity threshold.

FIG. 3 illustrates a criterion for crossing an absolute conductivity threshold. In this case, the processing unit is configured to determine that the electrical characteristic value crosses an absolute conductivity threshold defined by: $N_a \times Ds$, where Ds is a range of electrical characteristic values between minimum and maximum electrical conductivities of an entire range of electrical conductivities of the anatomical structure considered, and $N_a$ is a real number between 0 and 1. $N_a$ may be chosen to optimize the sensitivity and specificity of the detection, depending on the type of surgical procedure, and therefore expected tissues to be encountered, and in a way that works for a wide population of patients.

Preferably, the range of values of electrical characteristic Ds is the extent of the variation of the electrical conductivity between the first electrical conductivity of the first anatomical medium, e.g., soft tissues or blood assimilated to soft tissues with an acceptable approximation, and the third electrical conductivity of the third anatomical medium corresponds to a layer of internal cortical bone. This range may depend on the patient and the anatomical area considered. To establish the range, it is possible either to use published data on the electrical conductivity of tissues or use a learning method of the artificial intelligence type on collected data, or employ a calibration step based on separately contacting the patient's cortical bone and then the patient's blood. For example, an article entitled "Characterization of the electrical conductivity of bone and its correlation to osseous structure," by Balmer et al. in Scientific Reports (2018) 8:8601, describes conductivity values varying between approximately 9 mS/m for cortical bone and 230 mS/m for blood. A ratio of about 25 between the low value (cortical bone) and the high value (soft tissue, blood) is thus observed. In internal work carried out by the applicant using the PediGuard® device, the ratio between the highest and lowest resistance that the device was able to measure is 30, between 300 Ohms to 10 kOhms, which corresponds to electrical conductivities of about 50 milli-Siemens per meter to 1500 milli-Siemens per meter. The range of values of electrical characteristic Ds may therefore be up to 1500 milli-Siemens per meter. In other embodiments, depending on the anatomical structure considered, the range of electrical characteristic values may be empirically determined between the extreme values of the electrical characteristic in the set of anatomical media constituting the anatomical structure.

In addition, or in the alternative, a criterion for crossing a relative conductivity threshold may be employed. In this case, the processing unit is configured to determine that the electrical characteristic value crosses a relative conductivity threshold defined by: $N_r \times MA(d)$ where MA is an average of the electrical characteristic values A between an initial depth value do and a depth value d, and N r is a real number between 0 and 5. $N_r$ may be chosen to optimize the sensitivity and specificity of the detection, depending on the type of surgical procedure, the tissues expected to be encountered, and so as to cover a wide patient population.

Figure 4:
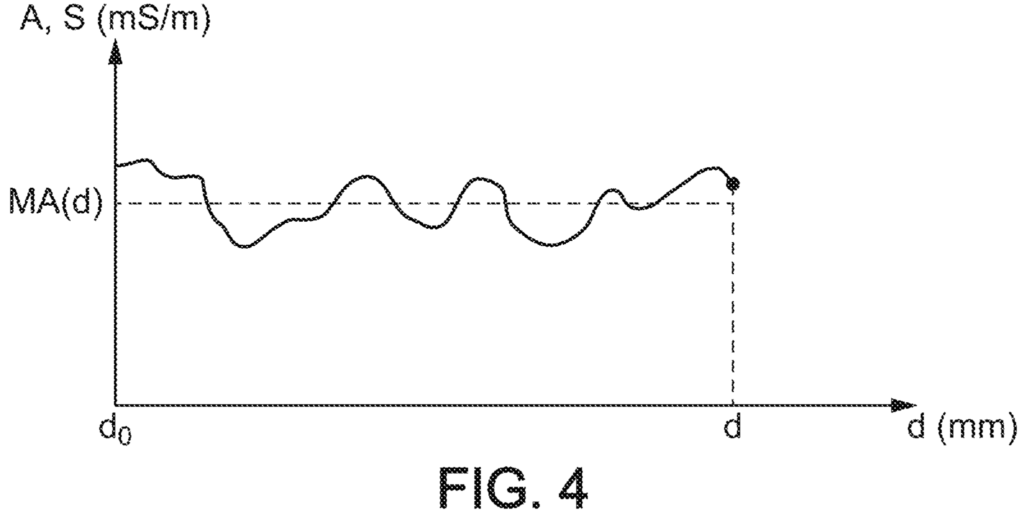
FIG. 4 is a graph depicting evolution of an electrical characteristic value as a function of depth to calculate an average of the electrical characteristic value between an initial depth and a current depth d for use in checking a criterion for crossing a conductivity threshold with a relative conductivity threshold.

FIG. 4 illustrates an exemplary method of determining an average of the values of electrical characteristic MA(d) between an initial depth value do and a current depth value d.

Figure 5:
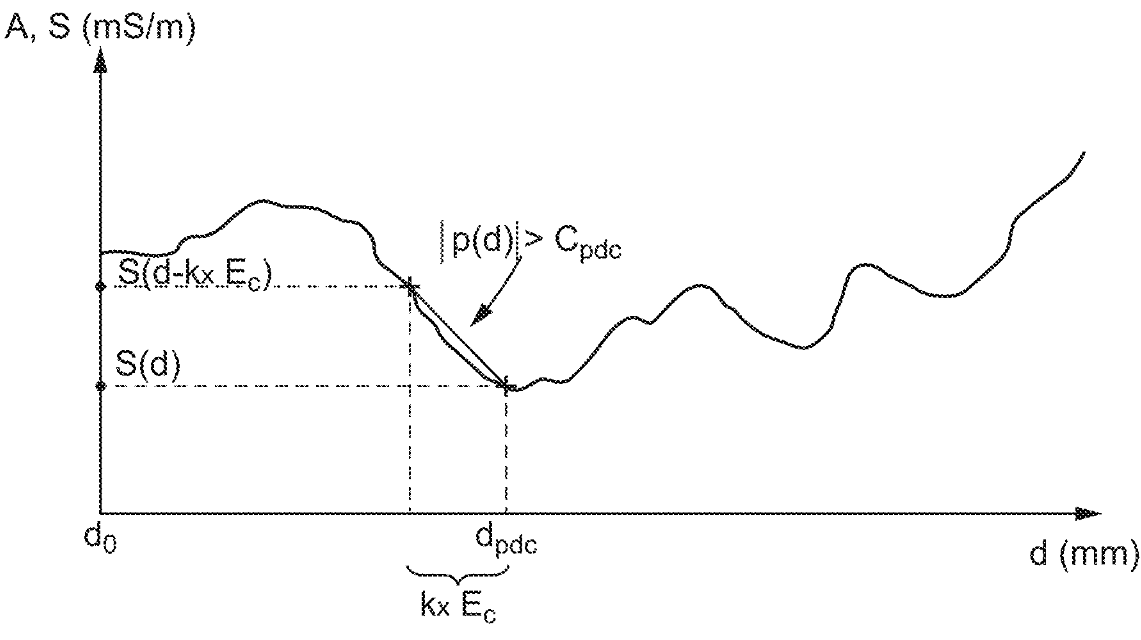
FIG. 5 is an alternative graph depicting evolution of an electrical characteristic value as a function of depth to calculate an average of the electrical characteristic value between an initial depth and a current depth d for use in checking a criterion for crossing a conductivity threshold with a relative conductivity threshold.

With respect to FIG. 5, during a drilling, a first drop in electrical conductivity may be observed, in which a first negative slope of electrical conductivity is encountered from the start of drilling and for which an absolute value is greater than a first descent slope of predetermined electrical conductivity $C_p d_c$, expressed in %. The depth value where this first slope of electrical conductivity is encountered is denoted $d_p d_c$.

Slope p(d) is the average slope in milli-Siemens per meter per millimeter (mS/m per mm) of the electrical conductivity of the material at drilling depth d over a range of depth variation which is of the order of magnitude of a thickness of the anatomical medium forming the interface, e.g., cortical bone. Thus, slope p(d) in milli-Siemens per meter per millimeter (mS/m per mm) is such that $$p(d) = \frac{T[A(d)] - T[A(d - k \times E_c)]}{k \times E_c}$$

where

T [A(d)] is the electrical conductivity in milli-Siemens per meter associated with transfer function T for the value of electrical characteristic A at depth d, T [A $(d-k\times E_c)$] is the conductivity electrical in milli-Siemens per meter associated with transfer function T for the value of electrical characteristic A at depth $d-k\times E_c$ located at a distance $k\times E_c$ from depth d, $E_c$ is a thickness of the inner cortical bone layer in millimeters, and k is a positive real number between 0 and 5.

The thickness of the cortical bone layer $E_c$ in the spine generally is between 1 mm and 3 mm.

Figure 6:
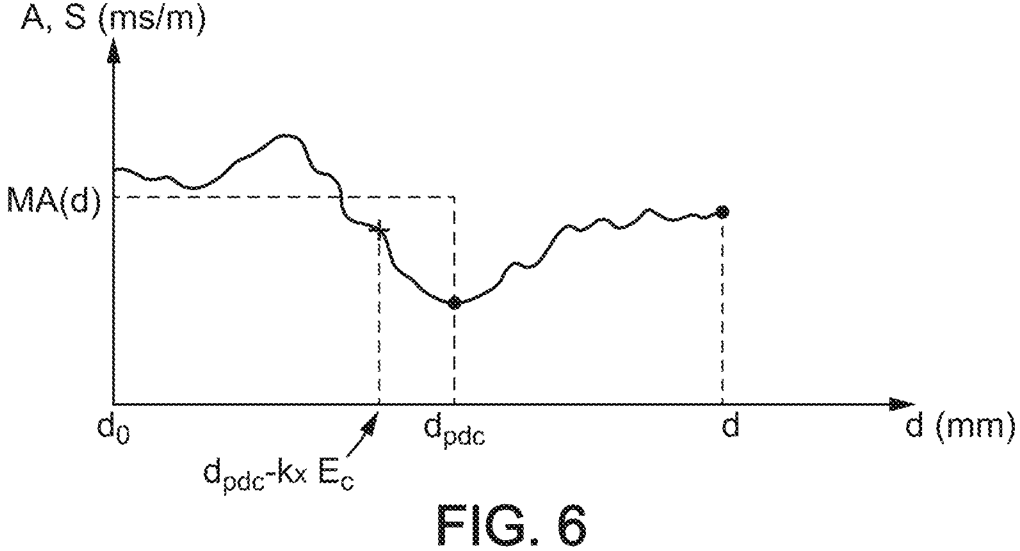
FIG. 6 is a further alternative graph depicting evolution of an electrical characteristic as a function of depth to calculate an average of the electrical characteristic value between an initial depth and a current depth d for use in checking a criterion for crossing a conductivity threshold with a relative conductivity threshold.

FIG. 6 shows a case in which a first conductivity drop is encountered before depth d, such that the range for averaging electrical conductivity values MA(d) is limited to the depth $[d_{pdc}-k\times E_c]$.

In addition or in the alternative, a criterion for crossing a critical conductivity gradient may be employed. In this case, the processing unit is configured to determine that at least the slope p(d) of the evolution of electrical characteristic values as a function of depth values crosses at least one critical conductivity gradient representative of a change of tissue between the first anatomical medium, e.g., soft tissue, and the third anatomical medium, e.g., cortical bone layer.

Figure 7:
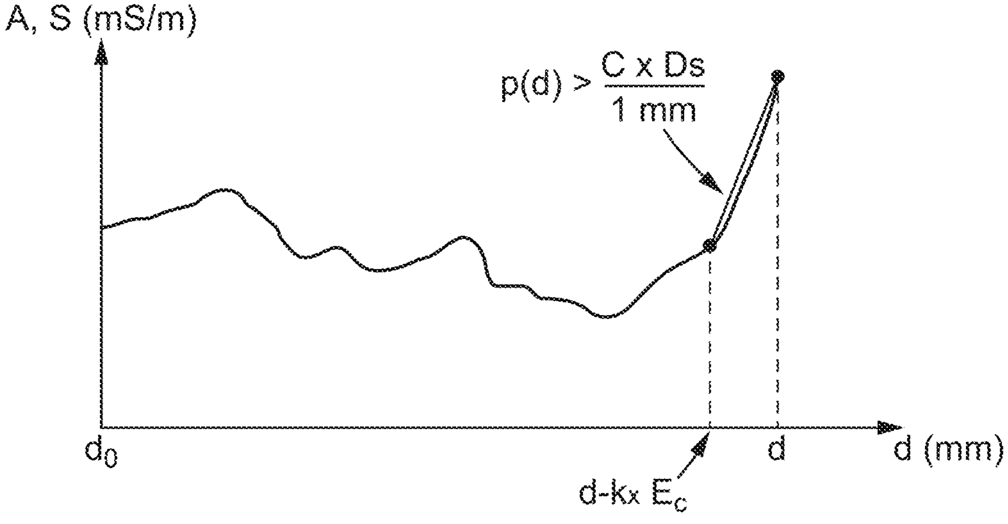
FIG. 7 is a graph depicting evolution of an electrical characteristic as a function of depth for use in verifying a criterion for crossing a critical conductivity gradient from a condition of increasing conductivity, a slope crossing, and exceeding, at least one critical conductivity gradient.

FIG. 7 illustrates a condition for increasing conductivity that makes it possible to verify the criterion for crossing the critical conductivity gradient. This condition is defined as:

$$p(d) > \frac{C \times Ds}{1 \text{ mm}}$$

where

C is a real number between 0 and 10.

Like $N_a$ and $N_r$, C may be chosen to optimize the sensitivity and specificity of the detection, depending on the type of surgical procedure, the tissues expected to be encountered, and to cover a wide patient population.

Thus, the criterion for crossing a critical conductivity gradient may be verified by detecting a significant upward slope in the sensed electrical characteristic.

By way of purely illustrative, non-limiting example, for C=15%, Ds=220 mS/m, $E_c$=2 mm, N=1.5, the warning signal is triggered at depth d if: [S(d)−S(d−1.5)]/3>15%×220/1 or P (d)>(33 mS/m)/1 mm.

Figure 8:
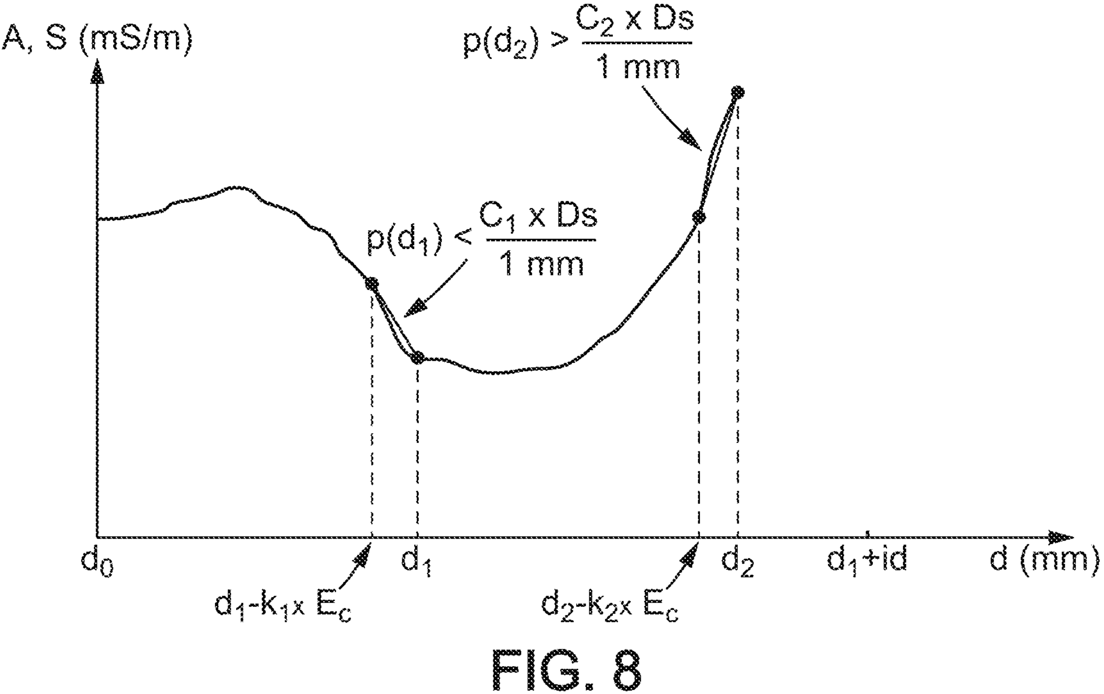
FIG. 8 is a graph depicting evolution of an electrical characteristic as a function of depth values for use in verifying a criterion for crossing a critical conductivity gradient from a condition of variation in conductivity, wherein a first descending slope is less than a first critical conductivity gradient, and a second rising slope is greater than a second critical conductivity gradient.

In addition or in the alternative, the criterion for crossing a critical conductivity gradient may be verified by detecting a variation in conduction, as depicted in FIG. 8:

$$p(d_1) < \frac{C_1 \times Ds}{1\text{ mm}}$$

and $$p(d_2) > \frac{C_2 \times Ds}{1\text{ mm}}$$

where $p(d_1)$ is the slope at a depth value $d_1$, $C_1$ is a real number between −10 and 0, $p(d_2)$ is the slope at a depth value $d_2$ greater than $d_1$, and $C_2$ is a real number between 0 and 10.

As discussed above, $C_1$ and $C_2$ preferably are chosen optimize the sensitivity and specificity of the detection, depending on the type of surgical procedure, and the expected tissues to be encountered, so as to work for a wide patient population.

This foregoing electrical conduction variation assumes detection of a significant downward slope at depth $d_1$ followed by detection of a significant upward slope at depth $d_2$.

To make the detection of an effective tissue change reliable and to avoid inaccurate triggering of the warning signal, it is possible to add a condition to depths $d_1$ and $d_2$. In particular, the processing unit may be configured to check for a conductivity variation if the depth values $d_1$ and $d_2$ have a maximum difference e such that e=m×$E_c$ where m is a positive real number between 0 and 80. Thus, the criterion for crossing a critical conductivity gradient is only verified if the depth $d_2$ at which the significant upward slope remains within a limited interval after the depth $d_1$ at which the significant downward slope has been detected. Beyond this interval, the detection of the significant downward slope at the depth $d_1$ is ignored.

By way of an illustrative, non-limiting example, a conductivity variation condition may be defined as follows: a downward slope of 15% of the range of electrical characteristic Ds over 2.5 mm, followed, at less than 3 mm from the depth at which this descending slope is detected, with a slope rising by 20% of the extent of the electrical characteristic Ds over 1.5 mm. Therefore, Ds=220 mS/m and $E_c$=2 mm, $C_1$=−15%, $N_1$=1.25, m=1.5, $C_2$=20% and $N_2$=0.75. The warning signal is triggered at depth $d_2$ if:

there is a depth $d_1$ where a downward slope is observed: $P(d_1)$<−15%×220 mS/m/1 mm or P $(d_1)$<(−33 mS/m)/1 mm, and $d_2$<$d_1$+3 mm, and $P(d_2)$>20%×220 mS/m/1 mm or $P(d_2)$>(44 mS/m)/1 mm.

In some embodiments, the processing unit may be configured to define a plurality of critical conductivity gradients as a function of the average of the electrical characteristic values MA.

Figure 9:
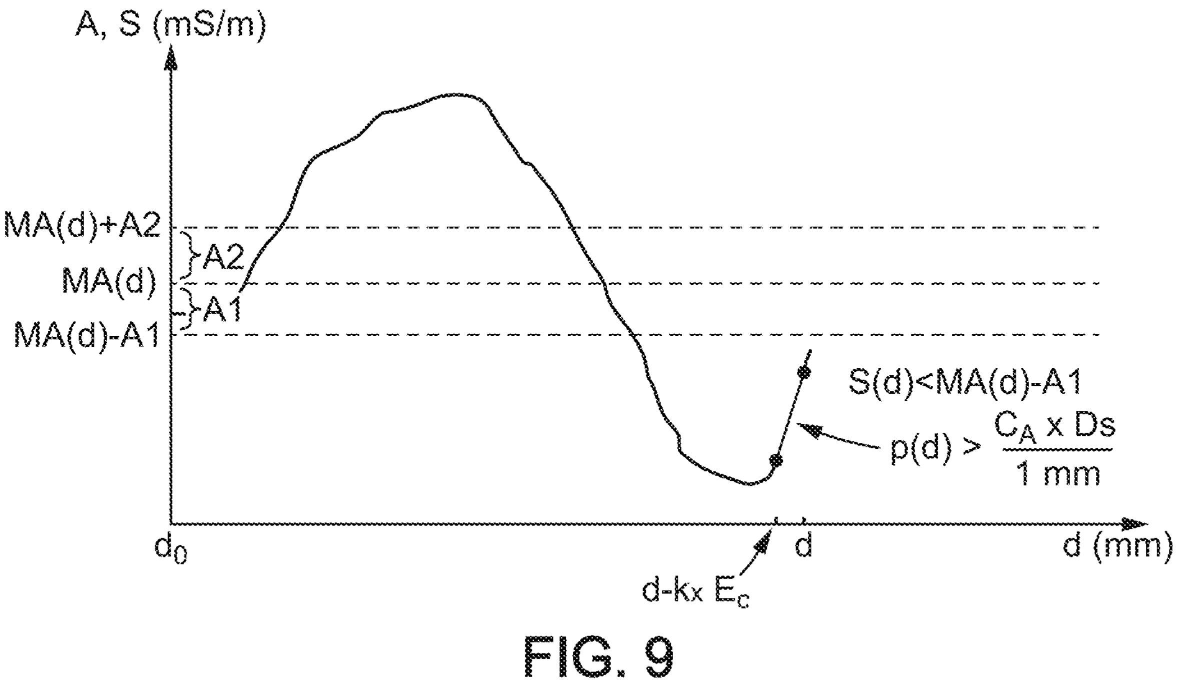
FIG. 9 is an example of a transfer function for use in verifying a criterion for crossing critical conductivity gradients that varies as a function of the average of the electrical characteristic values.
Figure 10:
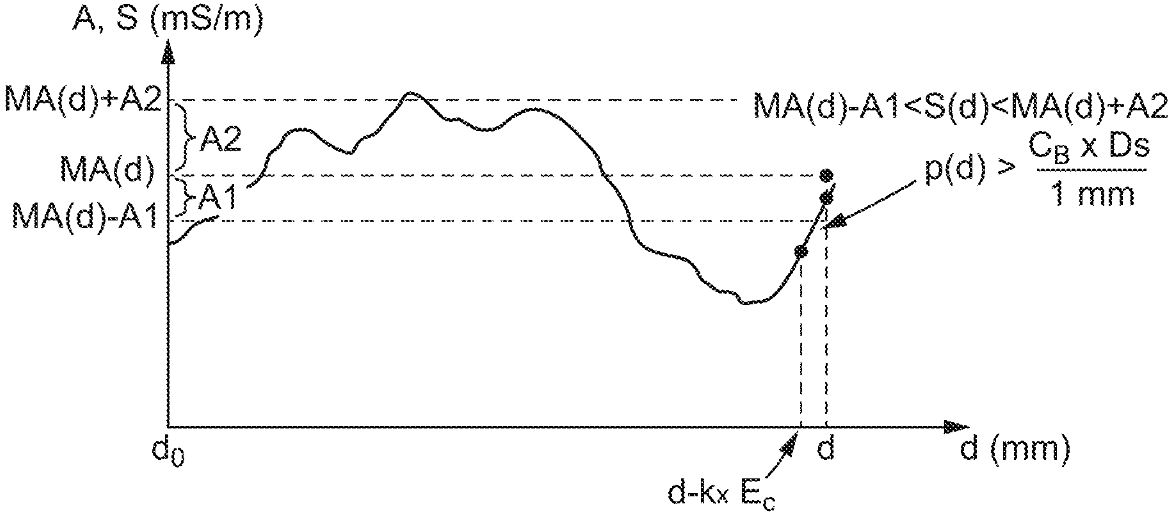
FIG. 10 is another example of a transfer function for use in verifying a criterion for crossing critical conductivity gradients that varies as a function of the average of the electrical characteristic values.

Referring now to FIGS. 9 and 10, critical conductivity gradients are described for distinct electrical conductivity domains.

In FIG. 9, if S(d)<[MA(d)−A1] where A1 is a chosen electrical conductivity value, the criterion for crossing the critical conductivity gradient is verified by detecting a first increase in conductivity such that: P (d)>$C_A$×Ds/1 mm where $C_A$ is a positive real number between 0 and 10, and in particular, between 0 and 1.

In FIG. 10, if S(d) is included in the interval [MA(d)−A1; MA(d)+A2], where A2 is a selected electrical conductivity value, the criterion for crossing the critical conductivity gradient is verified by detecting a second increase in conductivity such as: P(d)>$C_B$×Ds/1 mm where $C_B$ is a positive real between 0 and 10, and in particular, between 0 and 1.

Finally if S(d)>MA(d)+A2, the criterion for crossing the critical conductivity gradient may be verified by detecting a third increase in conductivity such as: P(d)>$C_C$×Ds/1 mm where $C_C$ is a positive real between 0 and 10, and in particular between 0 and 1.

By way of illustrative, non-limiting example, with Ds=220 mS/m, MS(d)=100 mS/m, A=20 mS/m, B=15 mS/m, $C_A$=25%, $C_B$=20%; $C_C$=15%, if S(d)=90 mS/m, S(d) is included in the interval [80; 115] and the warning signal is emitted if p(d)>20%×220/1 mm, i.e. if p(d)>(44 mSm)/mm. If S (d)=75 mS/m, S (d) is less than 80 therefore the warning signal is emitted if p (d)>25%×220/1 mm, i.e. if p(d)>(55 mSm)/mm The aforementioned criteria and conditions can be used alone or in combination, where appropriate by being weighted.

Since the warning signal indicates a significant change in electrical conductivity, representative of a change in tissue and therefore of a potentially risky situation, it may be used to modify the control signal controlling operation of the end effector or robotic arm. For example, at least one of the reversible actuators may be controlled by the processing unit to interrupt the drilling by imposing a zero setpoint force, by reducing the setpoint force, imposing a backward movement on the body, or redirecting axis L of the body in another direction. Rotary motion applied to the body also may be interrupted.

Processing unit 50 can be partially or completely integrated with one and/or the other of robotic arm 11 and penetrating medical device 25. Alternatively, processing unit 50 can be partially or totally remote. In the latter instance, processing unit 50 may include a communication interface establishing a link, wired or wireless, between its constituent units.

Although described in relation to medical system 10 having robotic arm 11 that provides a surgeon with assistance in controlling manipulation during a surgical intervention, the invention is not limited to this mode of operation. In particular, the inventive medical system could include any other medical device offering other types of assistance and, in particular, assistance without control of manipulation, but instead aimed solely at preventing the risk of injury or impairment of functional tissues.

Figure 11:
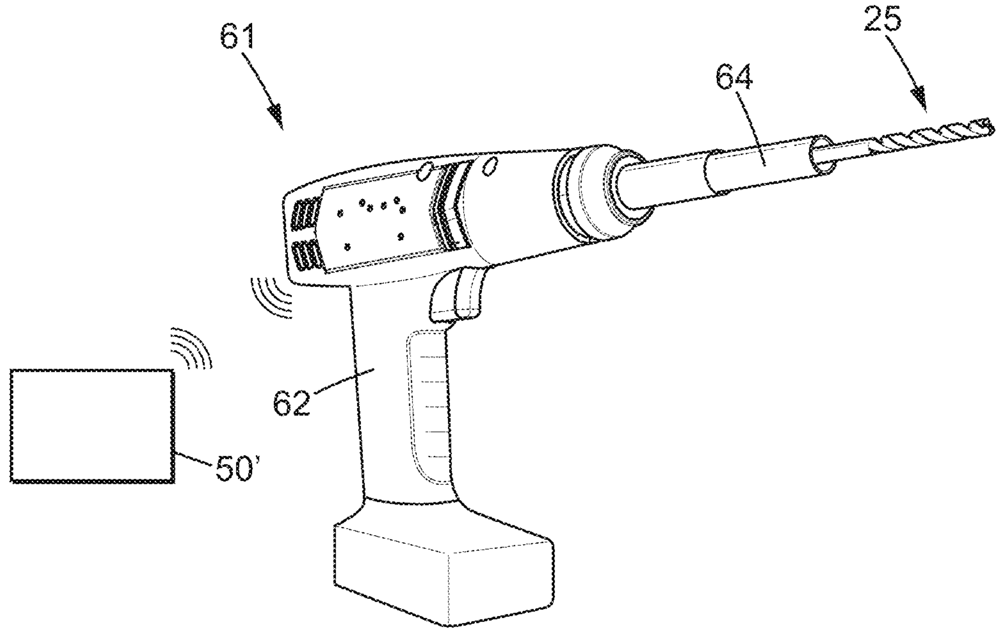
FIG. 11 is an alternative embodiment of a medical system of the present invention in which the penetrating medical device is mounted on a hand drill.

Referring now to FIG. 11, an alternative embodiment of a device constructed in accordance with the principles of the present invention is described. In the embodiment of FIG. 11, the medical device of the invention is embodied in a hand-held tool, i.e., base 62 is configured to form a handle held by an operator. In particular, the medical device is hand drill 61 comprising, in addition to base 62, effector member 64 formed by a chuck on which is mounted penetrating medical device 25 described above in relation to robotic arm 11 of first embodiment. Hand-held drill 61 is configured to allow rotational movement of effector 64 relative to base 62.

In the embodiment of FIG. 11, processing unit 50 may be at least partially remote, such that the medical device includes a communication interface to establish a wired or wireless connection between the drive member and the electrical measurement unit located in the base. The depth detection unit may be of an external type or consist of a graduation on the outer surface of body 26 or on a rod mounted near body 26 configured to slide parallel to penetrating medical device 25.

As described herein, the invention is configured for use in penetrating vertebra 1, corresponding to an anatomical structure including a bone structure and soft tissue exhibiting first, second and third electrical conductivities, such that the second electrical conductivity (of the soft tissues) is greater than the first. electrical conductivity (of the trabecular bone) and the third electrical conductivity (of the cortical bone) is lower than the first and second electrical conductivities. The invention is not however limited to such an anatomical structure. It also may be employed with any anatomical structure, bone or not, comprising at least first and second anatomical media having respectively first and second electrical conductivities, and optionally a third anatomical medium constituting an interface between the first and second anatomical media and having a third electrical conductivity.

For example, in an anatomical structure, between first and second anatomical media such that the second electrical conductivity is lower than the first electrical conductivity, the criterion for crossing the critical conductivity gradient may be verified with a condition of decrease in conductivity. This condition may be defined as follows:

$$p(d) < \frac{C' \times Ds}{1\ \text{mm}}$$

where

C' is a real number between −10 and 0.

Like C, C' may be chosen to optimize the sensitivity and specificity of detection, depending on the type of surgical procedure, and therefore the tissues expected to be encountered, and to work with a wide patient population.

Thus, the criterion for crossing the critical conductivity gradient may be verified if a significant downward slope is detected.

Moreover, in another anatomical structure comprising first, second and third anatomical media but in which the third electrical conductivity is greater than the first and second electrical conductivities, the criterion for crossing a critical conductivity gradient may be verified with a condition of conductivity variation such as:

$$p(d_1) > \frac{C_3 \times Ds}{1\ \text{mm}}$$

and $$p(d_2) < \frac{C_4 \times Ds}{1\ \text{mm}}$$

where $C_3$ is a real number between 0 and 10, $C_4$ is a real number between −10 and 0.

Like $C_1$ and $C_2$, $C_3$ and $C_4$ may be chosen to optimize the sensitivity and specificity of the detection, depending on the type of surgical procedure, and therefore the tissues expected to be encountered, and to work with a wide patient population.

The foregoing condition assumes detection of a significant upward slope at depth $d_1$ followed by the detection of a significant downward slope at depth $d_2$.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed is:

1. A medical device for penetrating an anatomical structure having multiple anatomical media with a range of electrical characteristics, the medical device comprising:

a body having a tip disposed at its distal end configured to penetrate into the anatomical structure, a first electrode having a first contact surface disposed at the distal end, a second electrode having a second contact surface disposed at the distal end and spaced apart from the first contact surface; and a processing unit operably coupled to the first electrode and the second electrode, the processing unit configured to:

store a set of criteria representative of an electrical characteristic of an anatomical medium as a function of depth in the anatomical medium;

measure an electrical characteristic of tissue disposed between the first contact surface and the second contact surface;

determine a critical gradient as at least one slope p(d) of an evolution of electrical characteristic values as a function of depth, representative of a change in a first anatomical medium towards a second anatomical medium;

detect, using the set of criteria, an electrical characteristic threshold from amongst an absolute threshold, a relative threshold, and the critical gradient; and emit a warning signal responsive to detection of the electrical characteristic threshold indicative of a predetermined transition between anatomical media.

2. The medical device of claim 1, wherein the anatomical structure includes bone and soft tissue, and the predetermined transition indicates actual or impending penetration of the tip into soft tissue corresponding to nervous tissue.

3. The medical device of claim 1, further comprising a robotic arm and end effector, and the processing unit further is configured to issue a control signal to the robotic arm or end effector responsive to detection of the electrical characteristic threshold indicative of a predetermined transition between anatomical media.

4. The medical device of claim 1, further comprising a robotic arm, end effector, and a force sensing unit, wherein the processing unit further is configured to issue a control signal to the force sensing unit to vary a force applied by the robotic arm or end effector responsive to detection of the electrical characteristic threshold indicative of a predetermined transition between anatomical media.

5. The medical device of claim 4, further comprising a depth detection unit, wherein the processing unit further is configured to receive a depth signal from the depth detection unit responsive to movement associated with respiration, and to issue a control signal to the force sensing unit responsive to the depth signal to control displacement of the end effector responsive to the movement associated with respiration.

6. The medical device of claim 1, further comprising a robotic arm, end effector, and a depth detection unit, wherein the processing unit further is configured to receive a depth signal from the depth detection unit, and to issue a control signal to the robotic arm or end effector responsive to detection of the electrical characteristic threshold indicative of a predetermined transition between anatomical media.

7. The medical device of claim 1, further comprising a robotic arm, end effector, and a depth detection unit, wherein the processing unit further is configured to receive a depth signal, and to control operation of the robotic arm or end effector in penetrating the anatomical structure responsive to the depth signal.

8. The medical device of claim 1, wherein the electrical characteristic of the anatomical medium is selected from amongst electrical conductivity, impedance, conductance, voltage, electrical intensity or a combination thereof.

9. The medical device of claim 1, wherein the processing unit is configured to determine the absolute threshold as $N_a \times Ds$, where Ds is the range of electrical characteristic values of the multiple anatomical media and $N_a$ is a real number between 0 and 1.

10. The medical device of claim 1, wherein the processing unit is configured to determine the relative threshold as $N_r \times MA(d)$ where MA is an average of the electrical characteristic values between an initial depth value and a current depth value d, and $N_r$ is a real number between 0 and 5.

11. The medical device of claim 1, wherein the at least one slope p(d) of the evolution of electrical characteristic values is computed as:

$$p(d) = \frac{T[A(d)] - T[A(d - kxE_c)]}{kxE_c}$$

where

T[A(d)] is an electrical conductivity associated by a transfer function T based on a value of an electrical characteristic A at depth d, $T[A(d-k\times E_c)]$ is an electrical conductivity associated by the transfer function T based on a value of electrical characteristic A at depth $d-k\times E_c$ located at a distance $k\times E_c$ of the depth d, $E_c$ is a thickness of an anatomical medium in millimeters, and k is a positive real number between 0 and 5.

12. The medical device of claim 11, wherein the processing unit is configured to verify the critical gradient based upon occurrence of either:

(a) an increase in conductivity if the second electrical conductivity is greater than the first electrical conductivity:

$$p(d) > \frac{C \times Ds}{1 \text{ mm}}$$

where

Ds is the range of electrical characteristic values for at least one of the anatomical media and C is a real number between 0 and 10, or (b) a decrease in conductivity if the second electrical conductivity is lower than the first electrical conductivity:

$$p(d) < \frac{C' \times Ds}{1 \text{ mm}}$$

where Ds is the range of electrical characteristic values for at least one of the anatomical media and C' is a real number between −10 and 0.

13. The medical device of claim 11, further configured to penetrate an anatomical structure comprising a third anatomical medium constituting an interface between a first anatomical medium having a first conductivity and a second anatomical medium having a second conductivity, the third anatomical medium having a third electrical conductivity, wherein the processing unit is configured to verify the critical gradient based upon occurrence of:

(a) if the third conductivity is lower than the first and second electrical conductivities $$p(d_1) < \frac{C_1 \times Ds}{1 \text{ mm}}$$

and $$p(d_2) > \frac{C_2 \times Ds}{1 \text{ mm}}$$

where $p(d_1)$ is a slope at a depth value $d_1$, $C_1$ is a real number between −10 and 0, $p(d_2)$ is a slope at a depth value $d_2$ greater than $d_1$, $C_2$ is a real number between 0 and 10, or (b) if the third conductivity is greater than the first and second electrical conductivities:

$$p(d_1) > \frac{C_3 \times Ds}{1 \text{ mm}}$$

and $$p(d_2) < \frac{C_4 \times Ds}{1 \text{ mm}}$$

where $C_3$ is a real number between 0 and 10, $C_4$ is a real number between −10 and 0.

14. The medical device of claim 13, wherein the processing unit is configured to check for a change in electrical characteristic if the depth values $d_1$ and $d_2$ have a maximum difference of e such that $e=m\times E_c$, where m is a positive real number between 0 and 80.

15. The medical device of claim 13, wherein the body is configured for use in penetrating an anatomical structure including a bone structure and soft tissue, wherein the bone structure has a layer of trabecular bone constituting the first anatomical medium and a layer of cortical bone constituting the third anatomical medium, and soft tissues constitute the second anatomical medium, the second electrical conductivity being greater than the first electrical conductivity and the third electrical conductivity being less than the first and second electrical conductivities.

16. The medical device of claim 15, wherein the body is configured to drill into the bone structure.

17. The medical device of claim 1, wherein the processing unit is configured to define a plurality of critical gradients based on average values of electrical characteristics of the multiple anatomical media.

18. The medical device of claim 1, wherein the body comprises a drill, a threaded tool, a screw, an implant, a needle, a cutting blade, a nail, an osteotome, a burr, a spindle, a probe, a square tip, a spatula, a curette and or a tap.

19. The medical device of claim 1, further comprising a base and an end effector, the body being mounted on the end effector, wherein the processing unit includes a force measurement unit configured to determine a force exerted on the body, and the processing unit is configured to control the displacement of the end effector relative to the base responsive to a setpoint force.

20. The medical device of claim 19, wherein the processing unit is configured to modify the setpoint force responsive to the warning signal.

21. The medical device of claim 1, wherein the medical device is embodied in a hand-held tool.

22. A method of penetrating an anatomical structure having multiple anatomical media with a medical device, the multiple anatomical media having a range of electrical characteristics, the medical device including a body having a tip disposed at its distal end configured to penetrate into the anatomical structure, a first electrode having a first contact surface disposed at the distal end, a second electrode having a second contact surface disposed at the distal end and spaced apart from the first contact surface, and a processing unit operably coupled to the first electrode and the second electrode, the method comprising:

storing in the processing unit a set of criteria representative of an electrical characteristic of an anatomical medium as a function of depth in the anatomical medium;

contacting the first contact surface and the second contact surface to the anatomical structure;

measuring an electrical characteristic of tissue disposed between the first contact surface and the second contact surface;

determining a critical gradient as at least one slope p(d) of an evolution of electrical characteristic values as a function of depth, representative of a change in a first anatomical medium towards a second anatomical medium;

detecting, using the set of criteria processed by the processing unit, a threshold amongst an absolute threshold, a relative threshold, and the critical gradient; and emitting from the processing unit a warning signal responsive to detection of the threshold indicative of a predetermined transition between anatomical media.

23. The method of claim 22, wherein determining the critical gradient as at least one slope p(d) of the evolution of electrical characteristic values as a function of depth comprises computing the at least one slope p(d) of the evolution of electrical characteristic values as:

$$p(d) = \frac{T[A(d)] - T[A(d - k \times E_c)]}{k \times E_c}$$

where

T[A(d)] is an electrical conductivity associated by a transfer function T based on a value of an electrical characteristic A at depth d, T[A(d−k×$E_c$)] is an electrical conductivity associated by the transfer function T based on a value of electrical characteristic A at depth d−k×$E_c$ located at a distance k×$E_c$ of the depth d, $E_c$ is a thickness of an anatomical medium in millimeters, and k is a positive real number between 0 and 5.

24. The method of claim 22, wherein the anatomical structure includes bone and soft tissue, and the detecting a threshold corresponds to detecting a predetermined transition indicative of actual or impending penetration of the tip into soft tissue corresponding to nervous tissue.

25. The method of claim 22, wherein the medical device further comprises a robotic arm and end effector, the method further comprising issuing a control signal, by the processing unit, to the robotic arm or end effector responsive to detection of the threshold indicative of a predetermined transition between anatomical media.

26. The method of claim 22, wherein the medical device further comprises a robotic arm, end effector, and a force sensing unit, the method further comprising issuing a control signal, by the processing unit, to the force sensing unit to vary a force applied by the robotic arm or end effector responsive to detection of the threshold indicative of a predetermined transition between anatomical media.

27. The method of claim 26, wherein the medical device further comprises a depth detection unit, the method further comprising receiving a depth signal from the depth detection unit responsive to movement associated with respiration, and issuing a control signal, by the processing unit, to the force sensing unit to control displacement of the end effector responsive to the depth signal.

28. The method of claim 22, wherein the medical device further comprises a robotic arm, end effector, and a depth detection unit, the method further comprising receiving a depth signal from the depth detection unit, and issuing, by the processing unit, a control signal to the robotic arm or end effector responsive to detection of the threshold indicative of a predetermined transition between anatomical media.

29. The method of claim 22, wherein the medical device further comprises a robotic arm, end effector, and a depth detection unit, the method further comprising receiving a depth signal, and controlling operation, by the processing unit, of the robotic arm or end effector to penetrate the anatomical structure responsive to the depth signal.

* * * * *